(12) United States Patent
Shertukde et al.

(10) Patent No.: US 11,583,194 B1
(45) Date of Patent: Feb. 21, 2023

(54) NON-INVASIVE ANGIOGRAPHY DEVICE

(71) Applicants: Hemchandra Madhusudan Shertukde, Simsbury, CT (US); Rekha Hemchandra Shertukde, Simsbury, CT (US)

(72) Inventors: Hemchandra Madhusudan Shertukde, Simsbury, CT (US); Rekha Hemchandra Shertukde, Simsbury, CT (US)

(*) Notice: Subject to any disclaimer, the term of this patent is extended or adjusted under 35 U.S.C. 154(b) by 0 days.

(21) Appl. No.: 16/825,797

(22) Filed: Mar. 20, 2020

(51) Int. Cl.
*A61B 5/00* (2006.01)
*A61B 5/022* (2006.01)

(52) U.S. Cl.
CPC ........ *A61B 5/02233* (2013.01); *A61B 5/6823* (2013.01); *A61B 5/6898* (2013.01); *A61B 5/7203* (2013.01); *A61B 5/7257* (2013.01); *A61B 2562/0204* (2013.01)

(58) Field of Classification Search
CPC . A61B 5/02233; A61B 5/7257; A61B 5/7203; A61B 5/6898; A61B 5/6823; A61B 2562/0204
See application file for complete search history.

(56) References Cited

U.S. PATENT DOCUMENTS

| | | | | |
|---|---|---|---|---|
| 4,770,184 | A | * | 9/1988 | Greene, Jr. ............ G16H 15/00 600/454 |
| 5,638,823 | A | * | 6/1997 | Akay .................... A61B 5/7264 600/501 |
| 5,687,738 | A | | 11/1997 | Shapiro et al. |
| 6,053,872 | A | | 4/2000 | Mohler |
| 6,178,386 | B1 | | 1/2001 | Shertukde et al. |
| 7,291,111 | B2 | | 11/2007 | Shertukde et al. |
| 7,527,597 | B2 | | 5/2009 | Sandler et al. |
| 8,055,333 | B2 | | 11/2011 | Duann |
| 8,750,971 | B2 | | 6/2014 | Tran |
| 8,968,195 | B2 | | 3/2015 | Tran |
| 10,984,644 | B1 | * | 4/2021 | Alsahlawi ............... G08B 21/02 |
| 2004/0186357 | A1 | * | 9/2004 | Soderberg ............ A61B 5/0013 600/300 |
| 2004/0260188 | A1 | | 12/2004 | Syed et al. |
| 2005/0038360 | A1 | * | 2/2005 | Shertukde .......... A61B 5/02007 600/586 |
| 2007/0055151 | A1 | * | 3/2007 | Shertukde .......... A61B 5/02007 600/437 |
| 2008/0004904 | A1 | * | 1/2008 | Tran ..................... A61B 5/0022 705/2 |
| 2009/0297011 | A1 | * | 12/2009 | Brunner ................ B25J 9/1697 382/132 |

FOREIGN PATENT DOCUMENTS

| | | |
|---|---|---|
| CN | 108577883 | 9/2018 |
| WO | WO1997007733 | 3/1997 |

* cited by examiner

*Primary Examiner* — Jacqueline Cheng
*Assistant Examiner* — Tho Q Tran (57) ABSTRACT

The present invention provides a non-invasive portable device and method for diagnosing an occlusion in coronary arteries of a patient. The diagnostic system includes a signal processor configured to receive signals from a group of acoustic sensors attached to the torso of a patient. The diagnostic device is configured with a processor to receive and generate an output on a display using a high end algorithm.

17 Claims, 8 Drawing Sheets

NON-INVASIVE ANGIOGRAPHY DEVICE

FIELD OF INVENTION

The invention is an electronic-based, non-invasive angiography device and methods for diagnosing stenosis in a patient's coronary artery. More specifically, the present invention determines the location of stenosis in a coronary artery of a patient. The device may further determine the location of occlusion in a coronary artery of a patient using non-invasive acoustic sensors.

BACKGROUND OF THE INVENTION

Coronary Artery Disease (CAD), the most common form of heart disease, causes impaired blood flow in the arteries that supply blood to the heart. The most common cause of CAD is vascular injury with cholesterol plaque buildup in the arteries, known as atherosclerosis. When one or more of the coronary arteries become wholly or partially blocked, the heart's blood supply gets restricted. Thus, it becomes necessary to detect blockages in the coronary arteries at an early stage so as to prevent the blockage from getting more significant.

Traditionally, the use of angiography technique was done for the detection. Moreover, angiography is an invasive technique that requires the insertion of a catheter affixed with a camera into a patient's coronary arteries to view the patient's arteries. While angiography has been used to detect CAD for a long time, such invasive techniques require making incisions in the patient's body, which could sometimes leave large wounds that are painful and take a long time to heal. Moreover, there is a risk of infection while operating invasively.

A U.S. Pat. No. 8,055,333, ('333 patent) assigned to Jeng-Ren Duann, discloses a non-invasive technique to detect and locate abnormal heart conditions. Significant limitations to the methods and techniques disclosed in the patent include the use of a sensor arrangement that comprises a 12-lead EKG set, which is quite bulky, and the time required to perform the process.

Another U.S. Pat. No. 7,291,111, ('111 patent) assigned to MedScanSonics Inc., discloses a non-invasive technique to diagnose and detect the location of stenosis in the coronary artery of a patient. The '111 patent is a lighter system than the '333 patent system; however, the technique disclosed still uses acoustic sensors and an electrical sensor to diagnose stenosis using a Wavelet Transform (WT) analysis.

To overcome the drawbacks of invasive surgery while also addressing the shortcomings of the above described prior art non-invasive techniques, a device using non-invasive techniques to diagnose and detect CAD is disclosed in our invention.

Embodiments of the present invention may use just four lightweight acoustic sensors and eliminate any reliance on the electrical sensor used by prior art devices. Further, at least some of the present invention's embodiments disclose techniques typically used to detect occlusions in the heartbeat's diastolic part using a signal processing algorithm employing a simple Fourier Transform (FT) analysis.

As noted above, numerous methods and systems have been developed in the prior art that are adequate for various purposes. However, even though these inventions may be suitable for the specific purposes to which they address, they would not be ideal for the purposes addressed by the present invention as previously described.

SUMMARY OF THE INVENTION

An objective of the present invention is to provide a non-invasive device for diagnosing an occlusion in the coronary arteries of a patient. More particularly, disclosed is a diagnostic device for detecting coronary artery stenosis in the diastolic part of the heartbeat. The diagnostic device includes an electronic device, a number of acoustic sensors, and a high-end signal processing algorithm. Moreover, the signal processing algorithm is configured to receive signals corresponding to a patient's heartbeat from the acoustic sensors. These sensors are placed at different known locations on the torso of the patient. The electronic unit is a portable device, either a personal computer on wheels (COW), a lunch box unit, a tablet, or a smartphone. The received signals are processed to estimate a position for an occlusion in the coronary arteries of the heart. The processing algorithm processes the received signals from the acoustic sensors and conducts a Fourier transform on the received signals.

The Fourier Transform provides frequency domain analysis of the received signals that enable the user to detect stenosis. Moreover, the device detects the accurate coordinates of stenosis in the diastolic part of the heartbeat. The Fourier Transform parameters associated with (a) the frequency of turbulence of all the sensor signals and (b) the maximum time value of the time signal of the 'R' part of the systolic part of the heartbeat are used to obtain estimates of the time delays of the arrival of the signals at all the sensors. Such aids in the estimate for the location of the stenosis.

A reference point/marker for a patient is chosen and can be any point (such as the navel) on the patient's torso. The acoustic sensors may be placed at different locations around the reference point, receive a patient's heartbeat, and output a combination of signals. The signals represent the heartbeat of the patient. A threshold amplitude-frequency range is set for identifying the signals to be evaluated. The signals are processed to determine an occlusion's existence and severity in one or more of the coronary arteries.

The signal processing algorithm also includes a method to determine the location of the occlusion. The signal processing algorithm measures the time delay between any two signals. A difference in the time of arrival of signals from any two sensors is indicative of a possible blockage causing less linear (less smooth) blood flow. A blockage or occlusion is indicated when the amplitude of one or more received signals is more than the set threshold amplitude. Signal processing may include amplifying, digitizing, synchronizing, and multiplexing of signals.

Once the signal processing algorithm processes the signals and a Fourier transform of the signals is conducted by the algorithm, the electronic display device displays the output, which shows the diagnoses results indicative of a blockage.

The signal processing algorithm is a high-level signal processing algorithm that evaluates a time difference of arrival (TDOA) and a Fourier transformation (FT) from the distinct outputs received by the electronic unit comprised in the COW. Wherein, the time difference of arrival (TDOA) and the Fourier transformation (FT) generate an eCAD coefficient for determining the error of variance in the diastolic region. The error of variance signifies that the occlusion is present or absent on the basis of the threshold level reached.

Another objective of the invention is to provide a non-invasive electro-acoustic sensing device that includes proprietary signal processing algorithms with fast DSP core hardware to detect and locate cardio and coronary vascular disease with almost pinpoint accuracy and in a very short time in real-time.

Yet another objective of the invention discloses an electro Cardiac Acoustic Device (eCAD) device, which comprises a computer on wheels (COW). Moreover, the distinctive feature of the invention is the use of a high-level signal processing algorithm. Also, a hardware set up that uses purely four acoustic sensors with signal analysis of the diastolic region only for evaluating stenosis. The invention only detects coronary artery occlusions.

Other objectives and aspects of the invention will become apparent from the following detailed description, taken in conjunction with the accompanying drawings, which illustrate, by way of example, the features in accordance with embodiments of the invention.

Embodiments of the present invention may employ any or all of the exemplary aspects above. Those skilled in the art will further appreciate the above-noted features and advantages of the invention together with other important aspects thereof upon reading the detailed description that follows in conjunction with the drawings, which illustrate, by way of example, the features in accordance with embodiments of the invention. The summary is not intended to limit the scope of the invention, which is defined solely by the claims attached hereto.

BRIEF DESCRIPTION OF DRAWINGS

Embodiments of the invention are described with reference to the following drawings, wherein.

DETAILED DESCRIPTION

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

As used in the claims, the definite article "said" identifies required elements that define the scope of embodiments of the claimed invention, whereas the definite article "the" merely identifies environmental elements that provide context for embodiments of the claimed invention that are not intended to be a limitation of any claim.

The present system relates to detecting deterioration in the blockage of the coronary arteries due to the formation of plaque and, more particularly, to a method for determining the early location of such blockages in the coronary arteries to enable cardiologists to accurately perform the angiogram to repair the blockages before a catastrophic failure of the heart. Currently, invasive procedures, known as angiograms, are some of the technologies used to diagnose the narrowing or blockage of the coronary arteries of the heart. The diagnostic tool eCAD is a non-invasive screening tool for assessing cardio and coronary conditions that can lead to myocardial infarctions.

The diagnostic tool is a non-invasive device for detecting coronary artery disease and erroneous functions of the heart valves to assess cardio fidelity. Normal biomedical signals like the systolic and diastolic motions of the heart are generally stationary. Coronary occlusions, however, create turbulence related to the diastolic motion, making these signals non-stationary, which can be detected acoustically. The acoustic signature of the turbulence can be studied using fractal analysis, and Fourier Transforms. The result is an estimation of an occlusion in the coronary arteries. The diagnostic tool primarily concentrates on the diastolic part of the heartbeat for the diagnosis of coronary artery occlusion.

Figure 1:
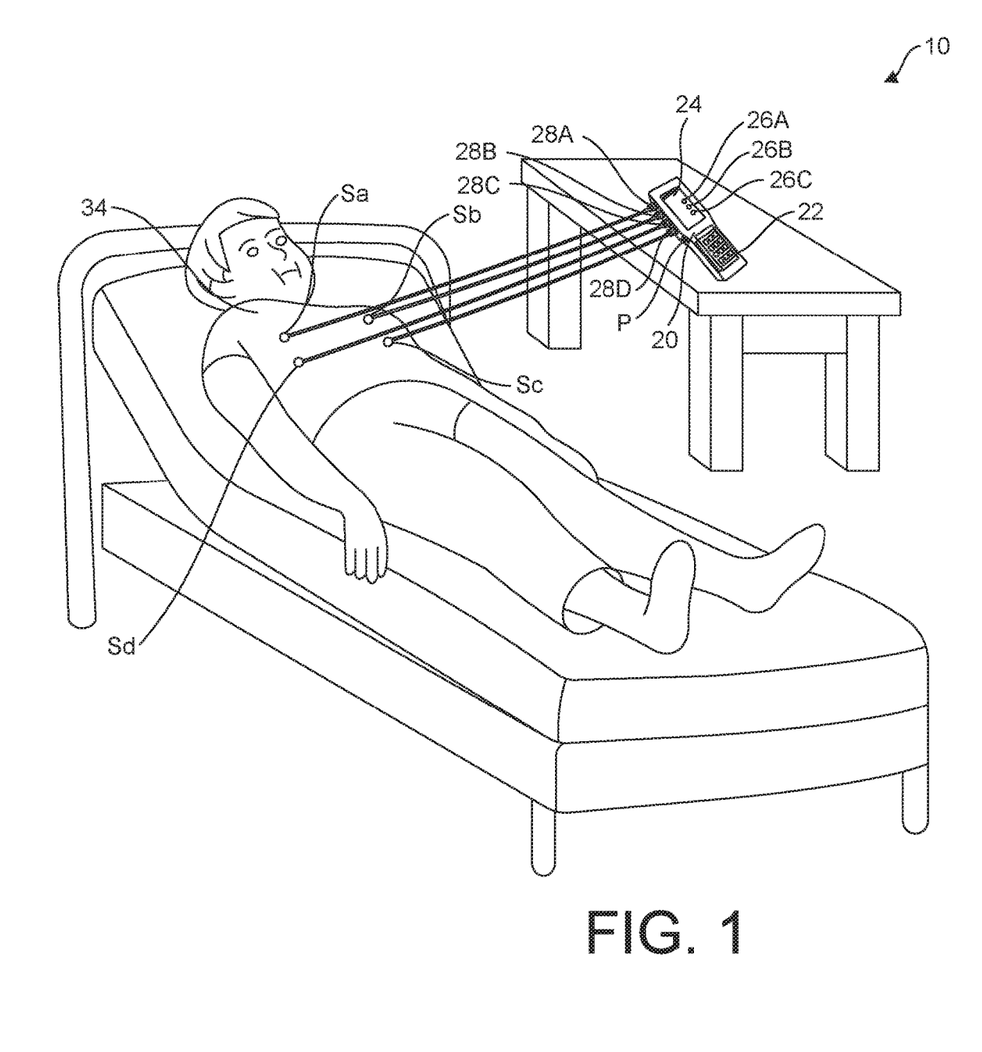
FIG. 1 illustrates a system for acquiring and analyzing acoustic signals in accordance with one embodiment of the invention.

FIG. 1 illustrates a system for acquiring and analyzing acoustic signals in accordance with one embodiment of the invention. The system 10 includes a diagnostic tool 20, and a plurality of acoustic sensors S. The diagnostic tool 20 is a handheld electronic device. The handheld electronic device 20 includes housing 22, a display screen 24, and a keyboard. The display 24 may be either of an LCD or LED screen with the length of the screen being of any suitable size (e.g., between 5-8 inches and width between 3-5 inches). A slot may be provided in the housing for receiving a memory card with non-volatile memory, typically a flash memory card, to store data in the electronic device 20. The handheld device 20 is a lightweight device that enables healthcare providers to communicate with a patient 34 in a better manner with as minimal movement as possible. A signal processor 26a may be configured within the electronic device to receive and process a plurality of acoustic signals. The handheld device 20 may comprise a plurality of ports 28. One end of each of a plurality of probes 30 (see FIG. 5a) may connect to a port 28 with the help of connectors 32. The opposing end of each of the probes 30 may connect to an acoustic sensor (Sa-Sd) placed at different known locations on the torso of the patient around a reference point for collecting input data.

The input data corresponds to the sounds of the heartbeat of the patient. The four acoustic sensors (Sa-Sd) use this input data to generate a plurality of acoustic signals as output that may feed to the signal processor 26a inside the electronic device 20.

The signal processor 26a may receive and process the acoustic signals 26b using a high-level signal processing algorithm 26c. What qualifies as a "high-level" signal processing algorithm is well known in the art. A threshold value of the amplitude and frequency of an acoustic signal 26b is predetermined and may be stored in a data file in a memory associated with the electronic device 20. The acoustic signals 26b received by the signal processor 26a may be evaluated and stored in another data file if the amplitude of each signal is greater than the set threshold.

The location of the acoustic sensors is noted with respect to a chosen origin on the torso of the patient. Examples of suitable reference points include the navel or some other convenient point. A high-level algorithm 26c may be configured to calculate the distance of each sensor S from the origin. The coordinates in 3-D of the origin are taken as (x0, y0, z0). Euclidean distance is calculated between each sensor (30a-d) (FIG. 5A) and the origin. This distance is noted, a time of arrival of each acoustic signal 26b is calculated by the algorithm, and real-time signals of the heartbeat captured. Corresponding time difference of arrival of the signals 26b is evaluated using the speed of sound for the medium inside the chest. Since this medium consists of tissue, bones, and blood, a typical value of the speed of sound in blood (water) is chosen as the closest known speed. Time taken by each acoustic signal to reach the reference point is known; thus, any deviation from the known value is considered abnormal and is indicative of an occlusion.

The high-level signal processing algorithm 26c is responsible for calculating the time difference of arrival (TDOA) for each acoustic signal, thereby providing an estimate of where the occlusion lies. The value of TDOA for each acoustic signal may be displayed on the screen 24. Further, the high-level signal processing algorithm 26c conducts a Fourier Transform on each output signal to determine the location of the stenosis. The transformed waves may be displayed on the screen 24 for diagnoses.

Figure 2:
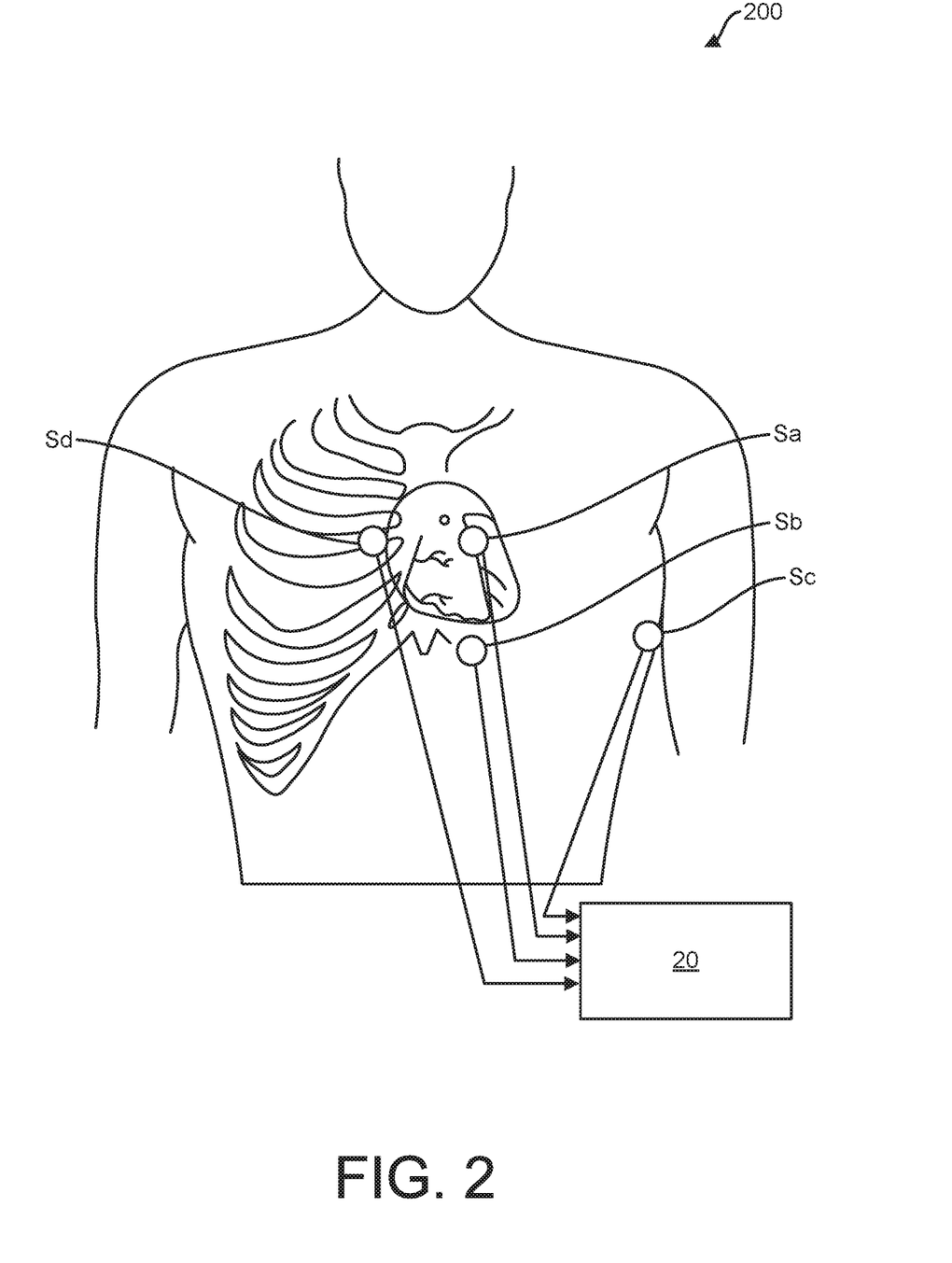
FIG. 2 illustrates the location of each of the four acoustic sensors on the torso of the patient with respect to a reference point.

FIG. 2 illustrates exemplary locations of each of the four acoustic sensors on the torso of the patient with respect to a reference point. The system includes a diagnostic tool 20 and a number of acoustic sensors (Sa-d). The handheld device 20 may be equipped with a plurality of ports (28a-d) disposed at any suitable location. One end of each of a plurality of probes (30a-d) may be connected to a port (28a-d) with the help of connectors. The other end of each of the probes (30a-d) may be connected to the four acoustic sensors (Sa-d). The acoustic sensors may be placed at different known locations (or predefined locations) on the torso of the patient 34 around a reference point for collecting input data. A "known" location is simply a location previously identified to provide the sound data required for the analysis. The input data corresponds to the sounds of the heartbeat of the patient. The four acoustic sensors (Sa-d) use this input data to generate a plurality of acoustic signals (26b) as output, which are fed to the signal processor (26) inside the electronic device (20).

The four acoustic sensors (Sa-d) may be placed on the torso of the patient 34. A reference point may be chosen on the chest of the patient around which the four sensors are attached at different known locations (a,b,c,d). The four sensors could include a microphone or any piezoelectric crystal capable of detecting heartbeat sounds. The location of the acoustic sensors is noted with respect to a chosen origin on the torso of the patient, this can be the navel or some other convenient point. The high-level algorithm is configured to calculate the distance of each sensor from the origin. The coordinates in 3-D of the origin may be taken as (x0, y0, z0). Euclidean distance may be calculated between each sensor and the origin. This distance is noted and time of arrival of each acoustic signal is calculated by the algorithm. Corresponding time difference of arrival of the signals is evaluated using the speed of sound for the medium inside the chest.

For example, a reference point R has coordinates (x0, y0, z0). A sensor is positioned at a point A, having coordinates (xa, ya, za). A second acoustic sensor is positioned at point B, having coordinates (xb, yb, zb). A third acoustic sensor is positioned at point C, having coordinates (xc, yc, zc) and a fourth sensor is positioned at point D, having coordinates (xd, yd, zd). As noted previously, such acoustic sensor placements should be locations on the torso of a patient previously known to provide a good point for intercepting the acoustical waves generated by the patient's heartbeat.

The Euclidean distance between each sensor and the reference point may be calculated using the following formula. The sensor coordinates with respect to the origin are in general: $(x_i, y_i, z_i)$; $i=1, 2, 3, 4$. For $i=1 \ldots, n$; $n=4$, the Euclidean distance is given as: $D = \sqrt{(x_i-x_0)^2 + (y_i-y_0)^2 + (z_i-z_0)^2}$ where $x_i$, $y_i$ and $z_i$ are the coordinates of the ith sensor. Using speed of sound in cartilage, and other media, the time taken by each signal to arrive at the reference point (origin) from the each of the sensors can be calculated using the formula: Time taken: Euclidean Distance/Speed of sound in the respective media.

A high-level signal processing algorithm 26c conducts a Fourier Transform on each of the acoustic signals 26b. Fourier transform is a well-known method that transforms a time-domain signal to a frequency-domain signal to obtain the frequency coefficients. The high-level signal processing algorithm conducts a Fourier Transform on each output signal to determine the location of the stenosis.

Figure 3:
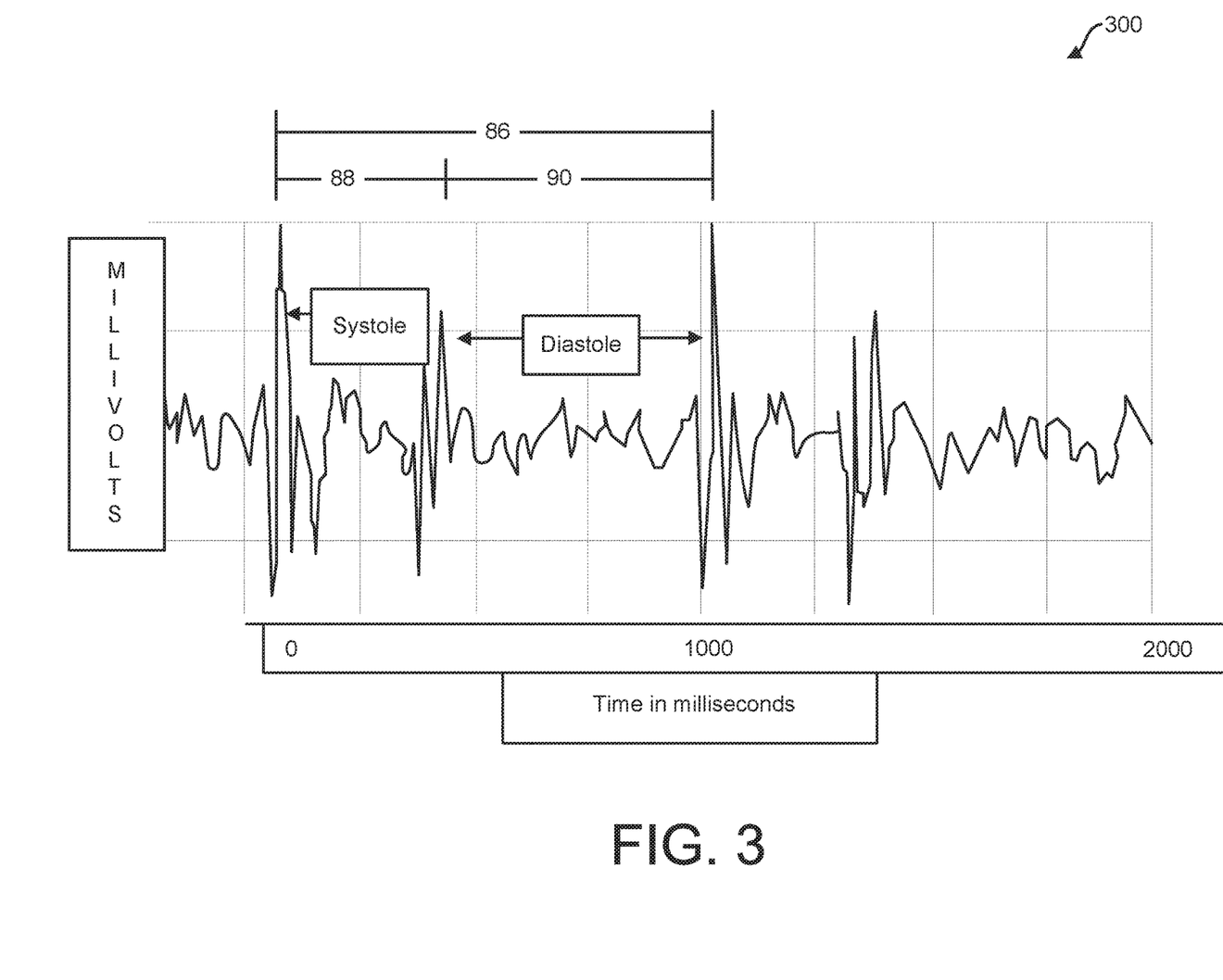
FIG. 3 illustrates a graph of a signal representing a typical heartbeat.

FIG. 3 illustrates a graph of a signal representing a typical heartbeat 300. A typical heartbeat signal wherein the sound of each heartbeat produces a heartbeat signal approximately 1000 milliseconds long. The heartbeat signal includes a systolic signal representing the systolic portion of the heartbeat signal related to the opening and closing of the valves and a diastolic signal representing the diastolic portion of the heartbeat signal, when the heart is quiet. The present invention diagnostic tool utilizes the diastolic signal for identifying a stenosis in the coronary arteries of a patient.

The diagnostic tool also determines the location (xs, ys, zs) of the stenosis. A coefficient is determined for characterizing the blockage. More specifically, an Electro Cardiac Acoustic Diagnostic Number for Coronary Artery Diagnostic Heart Occlusion Coefficient (eACDNCADHOC) number may be used to determine or representing an estimation of the degree of blockage in the artery caused by the stenosis.

Figure 4:
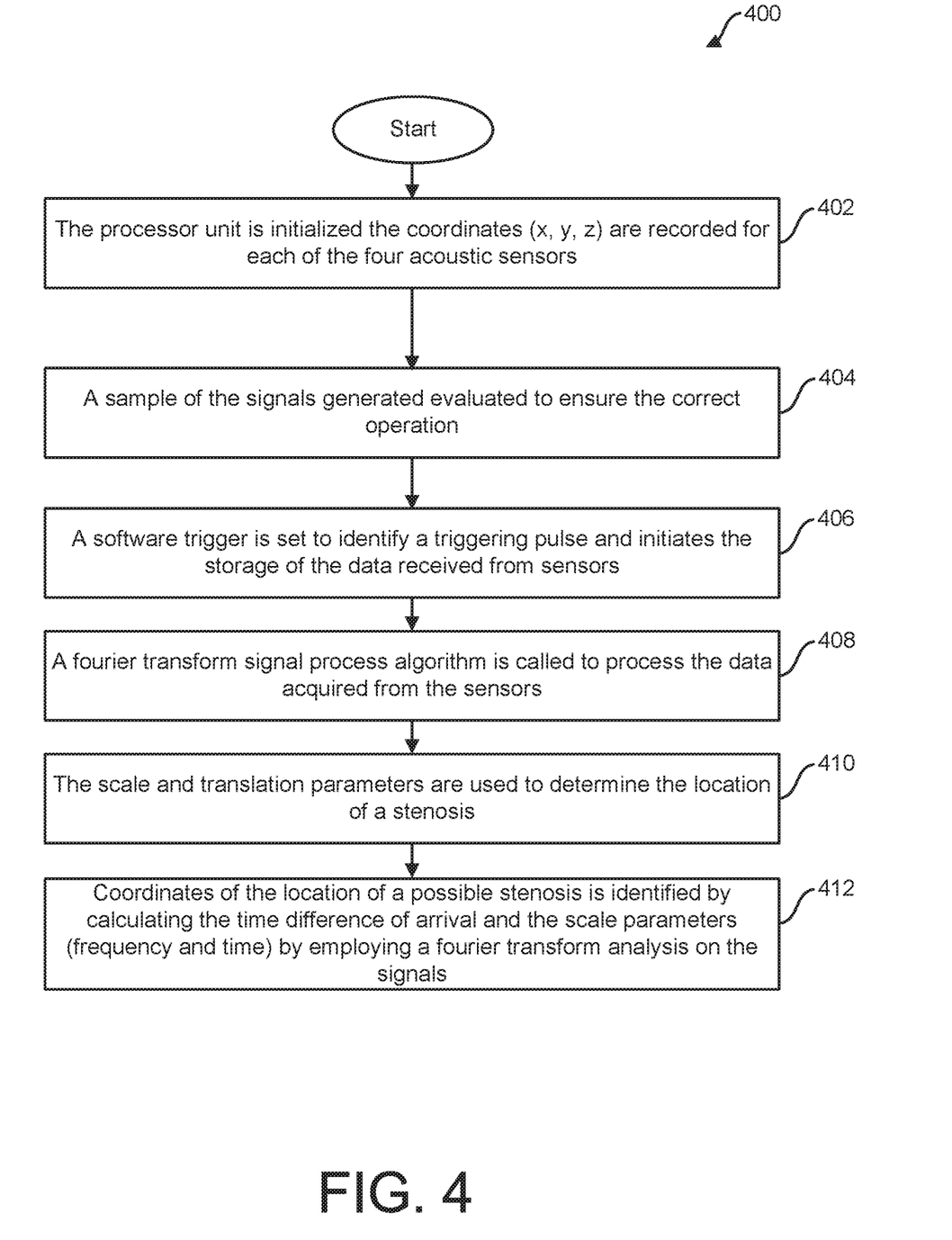
FIG. 4 illustrates a flowchart depicting the step by step functioning of the high-level signal processing algorithm.

FIG. 4 illustrates a flowchart depicting an exemplary step by step functioning of the high-level signal processing algorithm for determining the location and degree of a stenosis in one of the coronary arteries of the patient 400. When the processor unit has initialized the coordinates (x, y, z) may be recorded for each of the four acoustic sensors 402. A sample of the signals generated may be evaluated 404 to ensure the correct operation of the components of the diagnostic tool. The signals from each of the sensors may be sampled using a sample size for each sensor, and a data acquisition routine may occur. A software trigger may be set to identify a triggering pulse having an amplitude in excess of the threshold amplitude, which initiates the storage of the data received from sensors in a data buffer for further processing 406.

In one embodiment of the method of the invention, the patient is directed to hold his/her breath during a predetermined period of time for data acquisition, (e.g. 45-60 seconds). In a signal processing step, the multiplexed signals are passed into a data acquisition board, which samples signals in several channels simultaneously at a predetermined minimum sampling frequency per channel.

A Fourier transform signal process algorithm is called to process the data acquired from the sensors 408. The scale and translation parameters are used to determine the location of a stenosis 410. The coordinates of the location of a possible stenosis occurring at the point (xs, ys, zs) can be identified by calculating the time difference of arrival and the scale parameters (frequency and time) by employing a Fourier transform analysis on the signals 412.

All possible combinations of the signals from the sensors are processed using the Fourier transform process, and the corresponding time difference of arrival of the signals are evaluated knowing the speed of sound in the medium inside the chest. The eCAD number or coefficient of each sensor signal helps in depicting intensity of the constriction and TDOA helps in depicting the position of the occlusion. Since, the medium of the patient's chest, consists mainly of tissue, bones and blood, a typical value of the speed of sound in blood (water) is chosen as the closest known speed. For example, if the speed of sound in water is "c" feet/sec, then the location of the stenosis is determined by: $(x_s - x_i)2 + (y_s - y_i)2 + (z_s - z_i)2 = c \cdot 2 \cdot b \; 2$, i=A, B, C, D. The location (xs, ys, zs) of the stenosis in the coronary artery is estimated using 'MATLAB's symbolic logic toolbox, high level algorithm and the translation parameters.

Figure 5A:
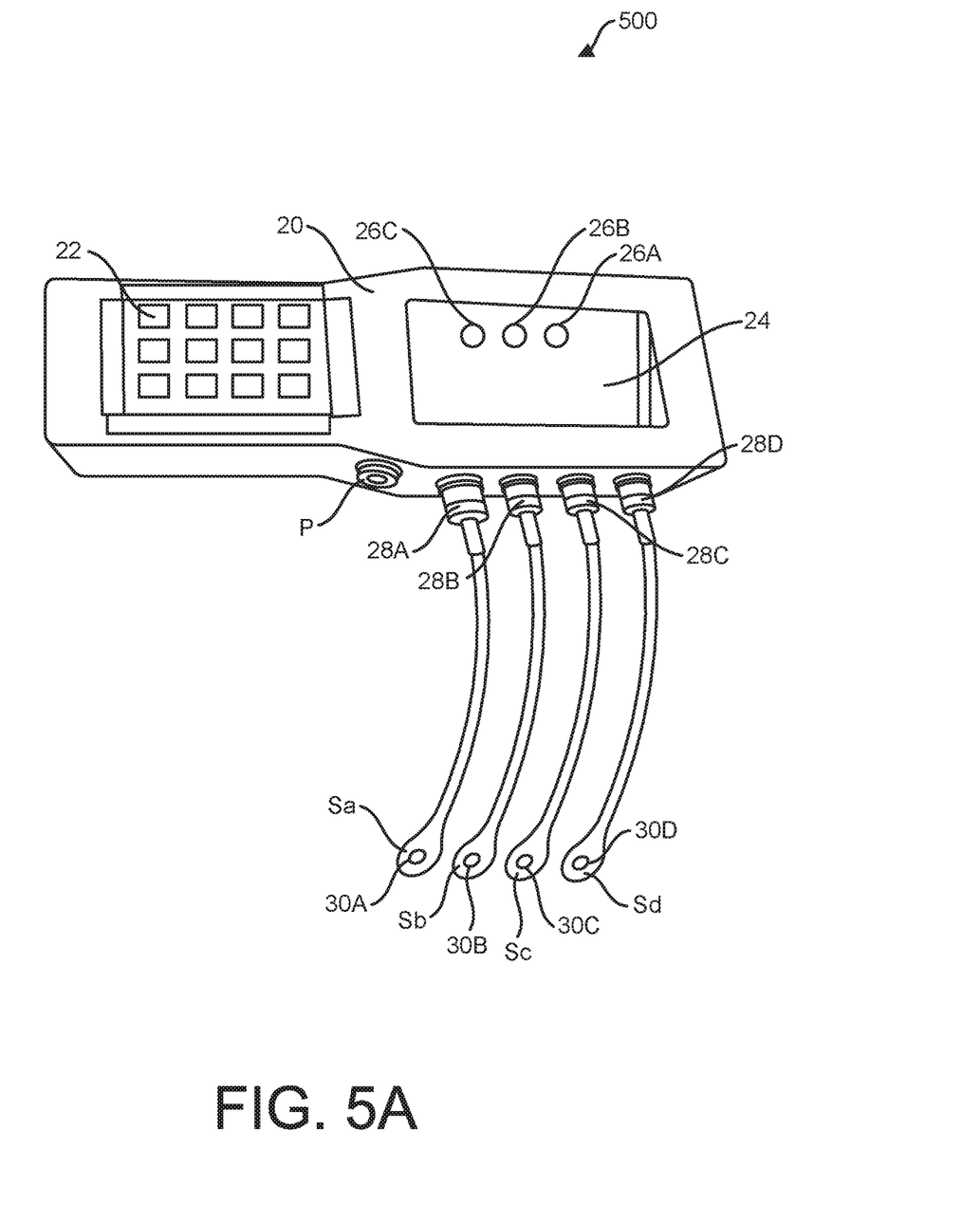
FIG. 5a illustrates the handheld diagnostic tool.

FIG. 5a illustrates the handheld diagnostic tool. The handheld device 20 is a lightweight device that enables healthcare providers to communicate with patients in a better manner with as minimal movement as possible. A signal processor 26a is configured within the electronic device 20 to receive and process a plurality of acoustic signals 26b and process it through Fourier transformation algorithm 26c. The handheld device 20 is equipped with a plurality of ports (28a-d) on one of its sides. One end of each of a plurality of probes (30a-d) is connected to the said ports with the help of connectors 32. The other end of each of the probes (30a-d) is connected to the four acoustic sensors (Sa-d) placed at different known locations on the torso of the patient around a reference point for collecting input data. The device 20 also includes a power input P for charging the device 20.

An exemplary user interface of the electronic device 20 comprises a screen 24. Screen 24 can be touch-sensitive. In the embodiment depicted, the user interface also comprises power status indicators, such as LEDs. In one embodiment, power status indicators can be incorporated into the screen. An audible on/off indicator can also be provided in embodiments.

Figure 5B:
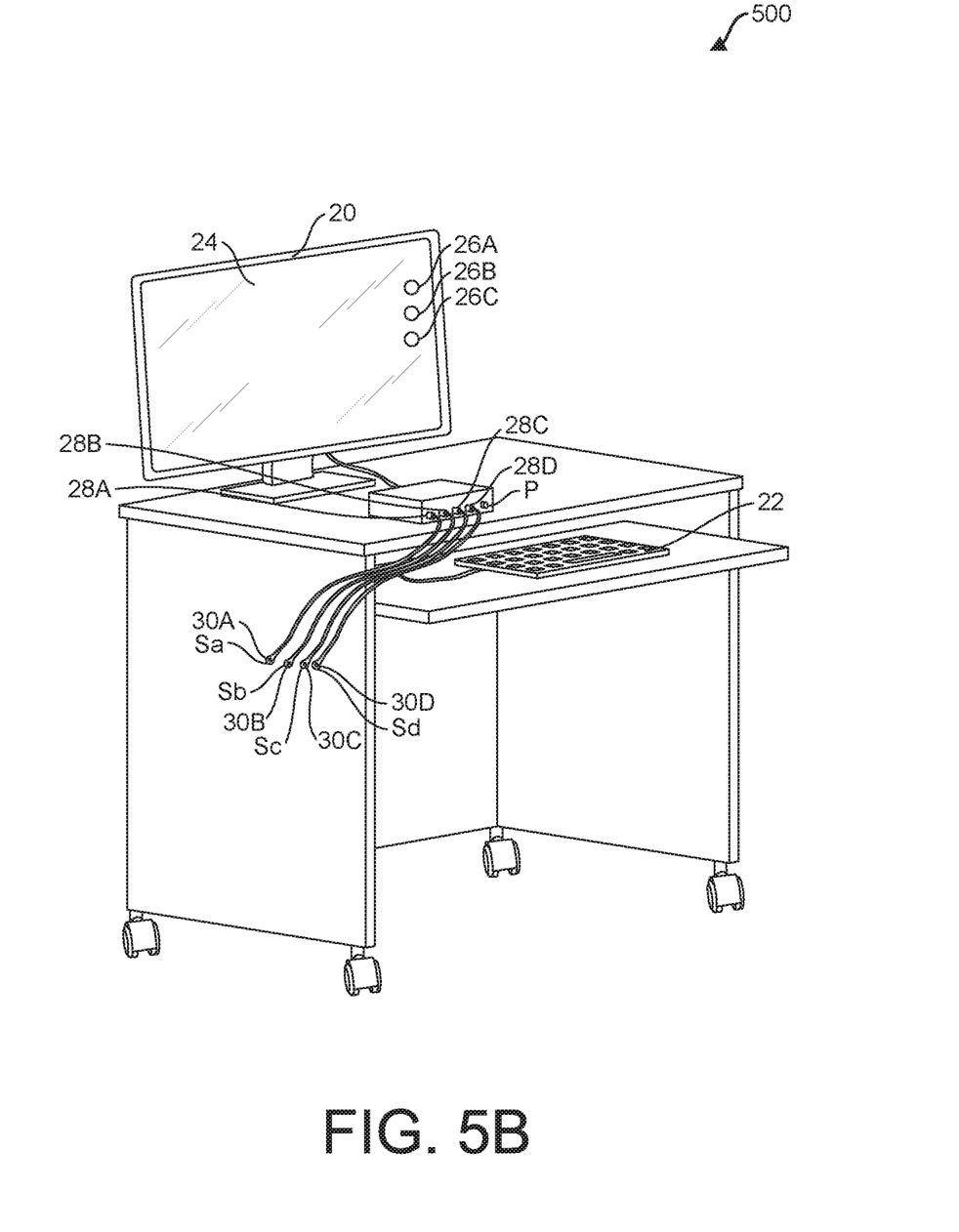
FIG. 5b illustrates an alternative diagnostic tool, a computer on wheels (COW)

FIG. 5b illustrates the alternative diagnostic tool comprising a computer on wheels (COW) 500. According to the alternative embodiment of the present invention, as shown in FIG. 5a, the COW 20 is an alternative to a handheld device that enables healthcare providers to communicate with patients in a better manner with as minimal movement as possible. A signal processor 26a is configured within the COW 20 to receive and process a plurality of acoustic signals 26b and process it through a Fourier transformation algorithm 26c. The COW 20 is equipped with an intermediary signal manipulator box 34 that may include a plurality of ports (28a-d). One end of each of a plurality of probes (32a-d) is connected to the said ports with the help of connectors. The other end of each of the probes (32a-d) is connected to the four acoustic sensors (30a-d) placed at different known locations on the torso of the patient around a reference point for collecting input data. The COW 20 is supplied with a power input P continuously or via a stand-alone rechargeable dc battery source.

The user interface of the COW 20 comprises a screen 24. Screen 24 can be a normal display or a tactile display. In the embodiment depicted, the user interface also comprises power status indicators, such as LEDs. For one embodiment, the power status indicators can be incorporated into the screen or some other portions of the COW 20. An audible on/off indicator can also be provided in embodiments. The final report of the patient is displayed on the screen 24 of the COW 20 after the processing of the Fourier transformation algorithm 26c.

Figure 6:
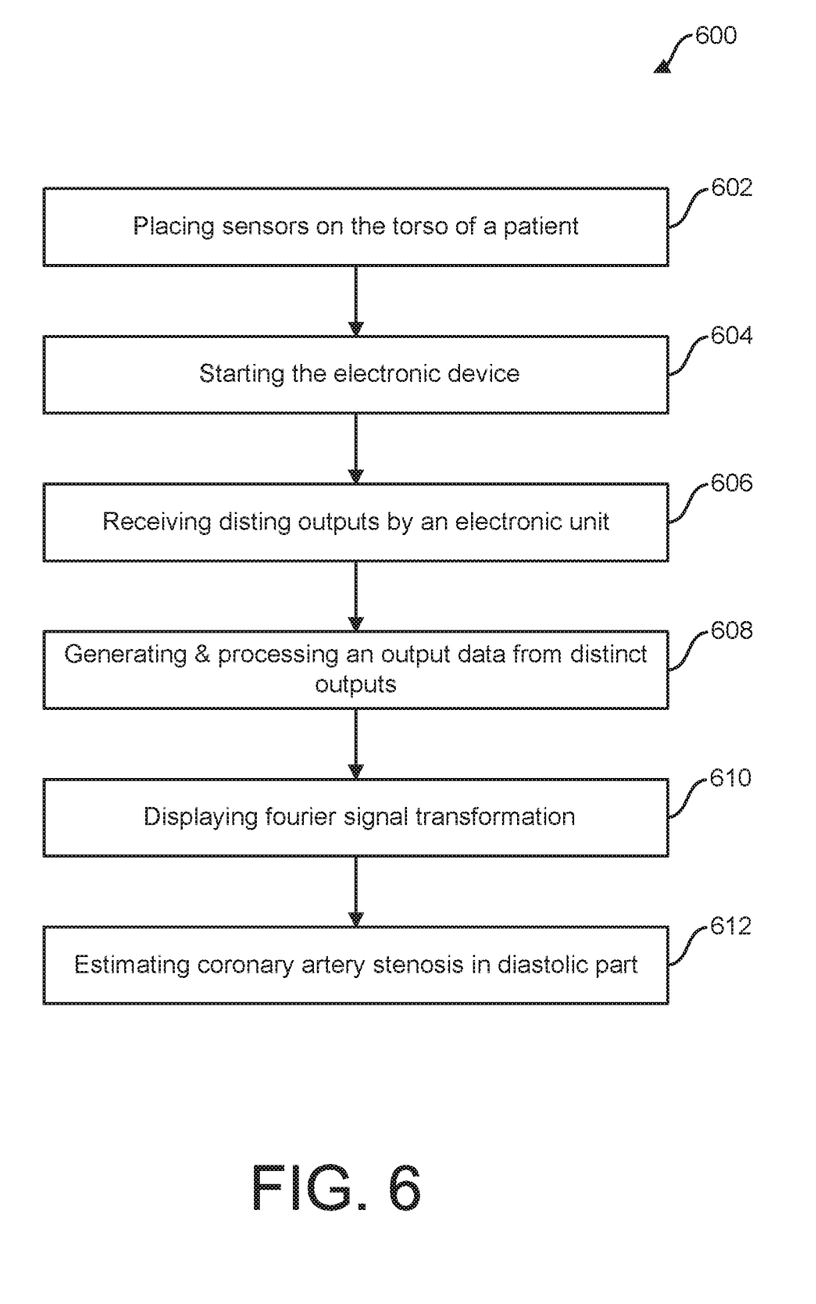
FIG. 6 illustrates a method of sensing coronary artery stenosis.

FIG. 6 illustrates a method of sensing coronary artery stenosis. A method of sensing coronary artery stenosis 600, the method includes the step of placing a group of four acoustic sensors on the torso of a patient 602. The placement of the multiple acoustic sensors generates distinct outputs based on the heartbeat of the patient. Ideally, as soon as the electronic device activates 604, it starts receiving the distinct outputs by an electronic unit 606, wherein the electronic unit is configured with a high-level signal processing algorithm. The high-level signal processing algorithm helps in generating and processing output data from the distinct outputs 608. Further, the output data is processed through the high-level signal processing algorithm to generate a Fourier signal transformation that may be displayed on the display screen 610, thereby estimating the coronary artery stenosis during the diastolic part of the heartbeat 612.

Figure 7:
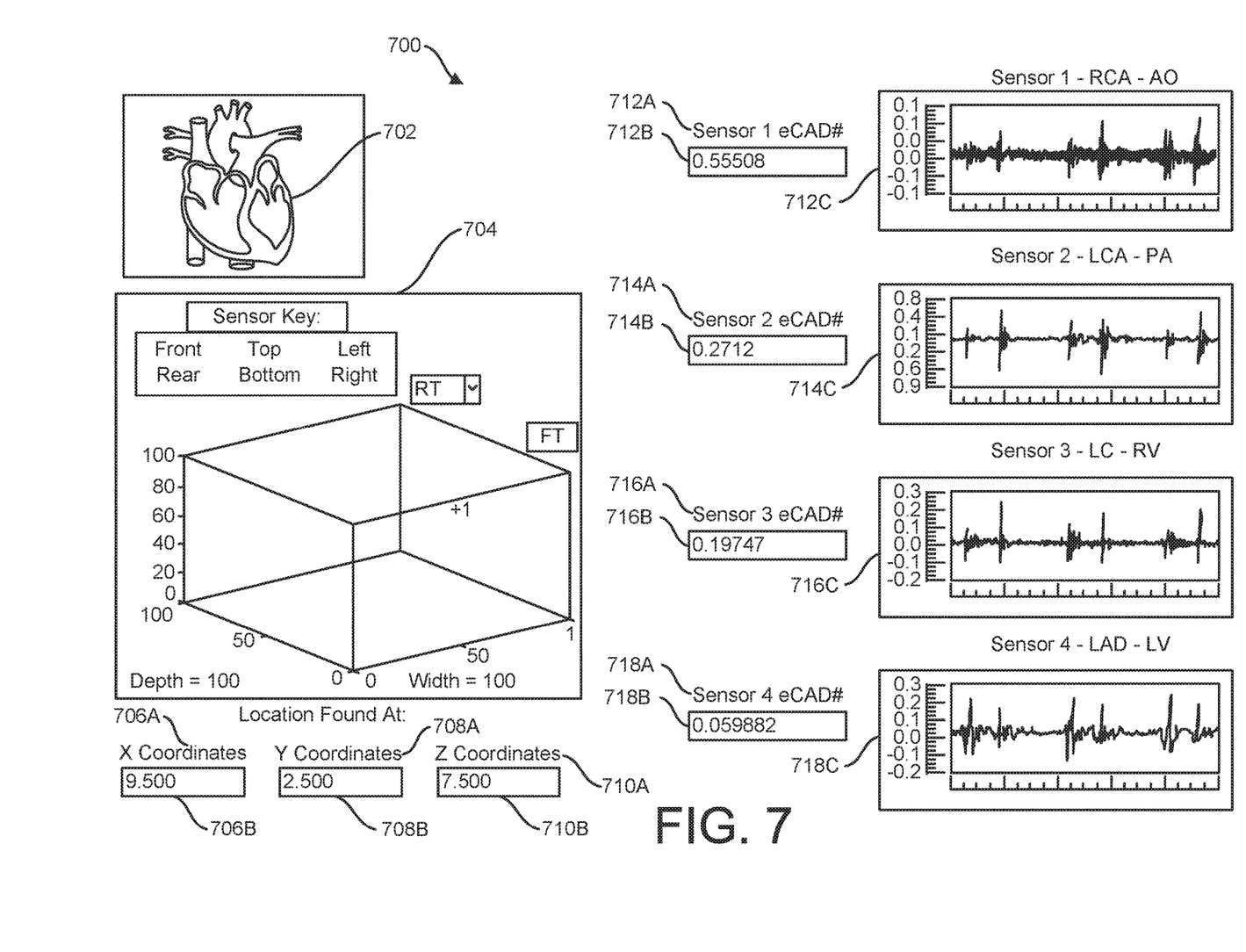
FIG. 7 illustrates a heart scan report.

FIG. 7 illustrates a heart scan report. The heart scan report 700 is displayed on the screen. The report may include a picture of heart 702, suggesting that the report is for heart scan. A graph 704 depicting the location of occlusion in x, y and z coordinates, wherein the sensor key shows all the side i.e. front, rear, top, bottom, left and right with the depth and width of the location. Embodiments may graph the x coordinate 706a, y coordinate 708a and z coordinate 710a with result values respectively for x coordinate 706b, y coordinate 708b and z coordinate 710b.

Moreover, the report also includes eCAD number value for all the four sensors. The four sensors involved are sensor 1 eCAD 712a with its value 712b and a graphical representation of sensor 1—right coronary artery—aorta (AO). A sensor 2 eCAD 714a with its value 714b and a graphical representation of sensor 2—left coronary artery—pulmonary artery (PA) 714c. Also, a sensor 3 eCAD 716a with its value 716b and a graphical representation of sensor 3—left coronary—right ventricle (RV) 716c. Moreover, a sensor 4 eCAD 718a with its value 718b and a graphical representation of sensor 4—left anterior descending (LAD) —left ventricular (LV) 718c is displayed. Afterward, the estimation of the presence of occlusion and its position is depicted through the report 700.

It will be appreciated that the various computer and processing systems and components discussed herein, for the electronic unit (as one example), are not limited to any particular hardware architecture or configuration. Embodiments of the methods and systems set forth herein may be implemented by one or more general-purpose or customized computing devices adapted in any suitable manner to provide the desired functionality. The device(s) may be adapted to provide additional functionality complementary or unrelated to the present subject matter, as well. For instance, one or more computing devices may be adapted to provide desired functionality by accessing logic or software instructions rendered in a computer-readable form. When software is used, any suitable programming, scripting, or another type of language or combinations of languages may be used to implement the teachings contained herein. However, software need not be used exclusively, or at all. For example, some embodiments of the systems and methods set forth herein may also be implemented by hard-wired logic or other circuitry, including, but not limited to, application-specific circuits. Of course, combinations of computer-executed software and hard-wired logic or other circuitry may be suitable, as well.

Embodiments of the systems and methods disclosed herein may be executed by one or more suitable computing devices. Such system(s) may include one or more computing devices adapted to perform one or more embodiments of the methods disclosed herein. As noted above, such devices may access one or more computer-readable media that embody computer-readable instructions which, when executed by at least one computer, cause the computer(s) to implement one or more embodiments of the methods of the present subject matter. Additionally, or alternatively, the computing device(s) may include circuitry that renders the device(s) operative to implement one or more of the methods of the present subject matter. Furthermore, components of the presently disclosed technology may be implemented using one or more computer-readable media. Any suitable computer-readable medium or media may be used to implement or practice the presently-disclosed subject matter, including, but not limited to, diskettes, drives, and other magnetic-based storage media, optical storage media, including disks (including CD-ROMs, DVD-ROMs, and variants thereof), flash, RAM, ROM, and other memory devices, and the like.

While, the various embodiments of the present invention have been described above, it should be understood that they have been presented by way of example only, and not of limitation. Likewise, the figure may depict an example architectural or other configuration for the invention, which is done to aid in understanding the features and functionality that can be included in the invention. The invention is not restricted to the illustrated example architectures or configurations, but the desired features can be implemented using a variety of alternative architecture and configurations.

Although, the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

The presence of broadening words and phrases such as "one or more," "at least," "but not limited to" or other like phrases in some instances shall not be read to mean that the narrower case is intended or required in instances where such broadening phrases may be absent.

The invention claimed is:

1. A non-invasive angiography device for sensing coronary artery stenosis and estimating the location of stenosis, said non-invasive angiography device comprising:
an electronic unit comprising:
a signal processor configured to execute signal processing algorithms;
a signal processing algorithm suitable for evaluating a plurality of sensor outputs; and
a display screen in communication with said processor;
a group of four acoustic sensors configured for being associated with the torso of a patient, wherein each said acoustic sensor generates a sensor output based on the patient's heartbeat;
wherein said signal processor is configured to receive the sensor output for each said acoustic sensor for at least the diastolic part of a heartbeat signal and use a first algorithm defined by said signal processing algorithm to define a valid output data file by performing threshold comparisons comprising comparing at least one of (a) the amplitude for the diastolic part of the heartbeat signal for each sensor output to a signal amplitude threshold value or (b) the frequency of at least part of said sensor output for each sensor output to a frequency threshold value, and generate a valid output data file comprising valid signals based at least in part on said threshold comparisons;
wherein said signal processor is further configured with a second signal processing algorithm to determine the presence of stenosis by calculating the Time Difference of Arrival (TDOA) value and determining an error of variance for the data in the valid sensor output data file and estimating the location of stenosis by generating a Fourier signal transformation for the data in the valid sensor output data file.

2. The non-invasive angiography device according to claim 1, wherein at least one of the four acoustic sensors is a microphone or a piezoelectric sensor.

3. The non-invasive angiography device according to claim 1, wherein the Fourier signal transformation generates the valid output data file for valid signals in the time domain and the frequency domain.

4. The non-invasive angiography device according to claim 1, wherein the electronic unit is either of a personal computer on wheels (COW), a lunch box unit, a tablet or a smart phone.

5. The non-invasive angiography device according to claim 1, wherein the signal processing algorithm is further used to locate the stenosis with respect to a three-dimensional view of the patient torso.

6. The non-invasive angiography device according to claim 1, further comprising means for removing all noise signals and locating coordinates of stenosis in the coronary arteries.

7. The non-invasive angiography device according to claim 1, wherein the signal processing algorithm utilizes a value for the speed of sound in at least one of cartilage, muscle, blood, and tissue for determining the TDOA values.

8. The non-invasive angiography device according to claim 7, wherein the reference point is located on the torso of the patient.

9. The non-invasive angiography device according to claim 1, wherein the time difference of arrival (TDOA) and the Fourier transformation (FT) generate an electro Cardiac Acoustic Device (eCAD) coefficient for determining error variance in the diastolic region of the heartbeat signal and wherein said eCAD coefficient is displayed by said display screen.

10. The non-invasive angiography device according to claim 9, wherein the error variance of 0.55 signifies stenosis is present.

11. The non-invasive angiography device according to claim 9, wherein the error variance of 0.05 signifies stenosis is absent.

12. A method of sensing coronary artery stenosis and estimating stenosis location, said method comprising the steps of:

placing a group of at least four acoustic sensors on the torso of a patient, wherein the at least four acoustic sensors each generate sensor outputs based on the patient's heartbeat;

configuring a signal processor to receive each of the sensor outputs for at least the diastolic portion of the patient's heartbeat;

configuring said signal processor with a first signal processing algorithm for processing and generating a valid sensor output data file from the sensor outputs using an amplitude threshold value or a frequency threshold value;

configuring said signal processor with a second signal processing algorithm to determine the presence of stenosis by calculating the TDOA value and determining an error of variance for the data in the valid sensor output data file and estimating the location of stenosis by generating a Fourier signal transformation for the data in the valid sensor output data file; and displaying at least one of a TDOA value and the Fourier signal transformation on a display screen for indicating the presence of coronary artery stenosis and estimating the location of coronary artery stenosis.

13. The method of sensing coronary artery stenosis and estimating its location according to claim 12, wherein the method is performed by one of a COW (Computer On Wheels) or handheld, non-invasive medical devices.

14. The method of sensing coronary artery stenosis and estimating its location according to claim 12, wherein the signal processing algorithm further locates the stenosis with respect to a three dimensional view of the patient torso.

15. A non-invasive angiography device for estimating the location of coronary artery stenosis, said non-invasive angiography device comprising:

an electronic unit means for evaluating a plurality of acoustic sensor outputs and displaying data derived from the plurality of acoustic sensor outputs;

a plurality of acoustic sensors configured to generate sensor outputs based on the patient's heartbeat;

wherein said electronic unit means is configured to receive the sensor output for each said acoustic sensor for at least the diastolic part of a heartbeat signal and use a first algorithm to compare the received sensor outputs to threshold values for each sensor output and generate a valid output data file based, at least in part, on the results of the comparison;

wherein said electronic unit means is further configured to use a second algorithm to determine the TDOA values for the data in the valid output data and generate a Fourier signal transformation of the data in the valid output data file to determine an error of variance signifying an occlusion is present and estimate the location of stenosis; and wherein said electronic unit means is further configured to display at least one of the TDOA values and the Fourier signal transformations.

16. The non-invasive angiography device according to claim 15, wherein said plurality of acoustic sensors comprises at least four acoustic sensors comprising at least one of a microphone or a piezoelectric device.

17. The non-invasive angiography device according to claim 15, wherein the Fourier signal transformations are in the time domain and the frequency domain.

* * * * *